United States Patent [19]

Gallay et al.

[11] Patent Number: 4,511,567

[45] Date of Patent: Apr. 16, 1985

[54] 6-[(4-SUBSTITUTED PIPERAZIN-L-YL)THIOCARBONYLAMINO]BENZAZOLES AND THEIR USE

[75] Inventors: Jean J. Gallay, Magden; Ernst Schweizer, Arlesheim, both of Switzerland

[73] Assignee: Ciba-Geigy Corporation, Ardsley, N.Y.

[21] Appl. No.: 418,955

[22] Filed: Sep. 16, 1982

Related U.S. Application Data

[63] Continuation-in-part of Ser. No. 262,569, May 11, 1981, abandoned.

[30] Foreign Application Priority Data

May 22, 1980 [CH] Switzerland ............ 4016/80

[51] Int. Cl.³ .............. C07D 417/12; C07D 413/12; A61K 31/495
[52] U.S. Cl. ................... 514/253; 544/368; 548/156; 548/217; 548/325
[58] Field of Search ............ 544/368; 424/250

[56] References Cited

U.S. PATENT DOCUMENTS 3,646,049  2/1972  Hoff et al. ............... 544/370
3,849,431  11/1974  Gallay et al. ............. 544/368

Primary Examiner—Donald G. Daus
Assistant Examiner—S. A. Gibson
Attorney, Agent, or Firm—Irving N. Feit

[57] ABSTRACT

The invention relates to a process for the manufacture of novel benzazole derivatives of the formula I

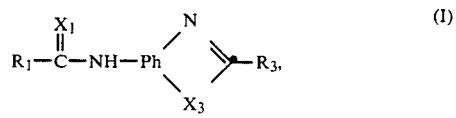

in which
R₁ represents an optionally 4-substituted piperazino group or a group of the formula R₂—alk—X₂—,
R₂ represents optionally esterified carboxy or represents hydroxymethyl,
alk represents lower alkylene or lower alkylidene,
X₁ and X₂, independently of one another, each represents oxygen or sulphur,
Ph represents 1,2-phenylene optionally substituted as well as by the group R₁—C(=X₁)—NH—,
X₃ represents oxygen, sulphur or optionally substituted imino, and
R₃ represents optionally fluorine-substituted lower alkyl or cycloalkyl,
and their salts.

The compounds of the formula I, which have proved to be excellent micro- and macrofilaricides and schistosomacides, are manufactured according to methods known per se.

24 Claims, No Drawings

6-[(4-SUBSTITUTED PIPERAZIN-L-YL)THIOCARBONYLAMINO]BENZAZOLES AND THEIR USE

This is a continuation-in-part application of our copending patent application Ser. No. 262,569, filed May 11, 1981, now abandoned.

The invention relates to novel benzazole derivatives of th formula I

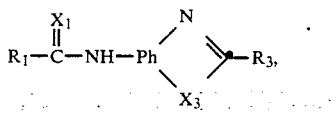

in which
$R_1$ represents an optionally 4-substituted piperazino group or a group of the formula $R_2$—alk—$X_2$—,
$R_2$ represents optionally esterified carboxy or represents hydroxymethyl,
alk represents lower alkylene,
$X_1$ and $X_2$, independently of one another, each represents oxygen or sulphur,
pH represents 1,2-phenylene optionally substituted as well as by the group $R_1$—C(=$X_1$)—NH—,
$X_3$ represents oxygen, sulphur or optionally substituted amino, and
$R_3$ represents optionally fluorine-substituted lower alkyl or cycloalkyl,
and their salts, processes for their manufacture, pharamceutical preparations containing them, and their use.

There come into consideration as substituents of piperazino $R_1$, for example, lower alkyl optionally substituted by hydroxy in a position higher than the α-position, for example in the 4-position of 4-lower alkylpiprazino, and oxido. Piperazino optionally substituted in the 4-position is accordingly, for example, 1-piperazino, 1-(4-lower alkyl)-piperazino or 1-(4-lower alkyl-4-oxido)-piperazino, or 1-[4-(hydroxy-lower alkyl)]-piperazino in which the hydroxy group is bonded in a position higher than the α-position.

Esterified carboxy is, for example, lower alkoxycarbonyl.

There come into consideration as additional substituents of Ph, for example lower alkyl, lower alkoxy, lower alkanoyl, trifluoromethyl and/or halogen.

Optionally substituted imino is unsubstituted imino or imino substituted, for example, by oxido, by an optionally substituted lower alkyl, phenyl-lower alkyl or phenyl radical, by lower alkenyl or lower acyl, such as lower alkanoyl, by lower alkoxycarbonyl, lower alkanesulphonyl, mono- or di-lower alkylcarbamoyl, or by alkylenecarbamoyl or 3-aza-, 3-oxa- 3-thia-alkylenecarbamoyl each having from 5 to 8 ring members. There come into consideration as substituents of lower alkyl therein, for example di-lower alkylamino groups and, as substituents of phenyl or of the phenyl radial of phenyl-lower alkyl, for example lower alkyl, lower alkoxy and/or halogen. Substituted imino is accordingly, for example, lower alkylimino, lower alkenylimino, phenyl- or phenyl-lower alkylimino each optionally substituted as stated, lower alkanesulphonylimino, mono- or di-lower alkylcarbamoylimino, or by alkylenecarbamoylimino or 2-aza-, 3-oxa- or 3-thia-alkylenecarbamoylimino each having from 5 to 8 ring members.

Cycloalkyl is, for example, 3- to 8-membered cycloalkyl, such as cyclopentyl, cyclohexyl or cycloheptyl, and also cyclopropyl, cyclobutyl or cyclooctyl.

Hereinbefore and hereinafter there are to be understood by "lower" organic radicals, for example those having up to and including 7, preferably up to and including 4, carbon atoms (C-atoms).

Lower alkyl may be straight-chain or branched and bonded in any position and, in the case of $R_1$, represents preferably straight-chain lower alkyl bonded by a secondary C-atom or branched, preferably α- or β-branched, lower alkyl, and otherwise represents preferably straight-chain lower alkyl bonded by a primary or secondary C-atom. Lower alkyl bonded by a primary C-atom is, for example, methyl, ethyl, 1-propyl, 1-butyl or 1-(1-methyl)-butyl, or/and also 1-pentyl, 1-hexyl or 1-heptyl. Straight-chain lower alkyl bonded by a secondary C-atom is, for example, 2-propyl or 2-butyl, 2- or 3-pentyl, 2- or 3-hexyl or 2-, 3- or 4-heptyl. Branched lower alkyl is, for example, tertiary butyl or isobutyl, or 2-(2-methyl)-butyl, 3-(3-methyl)-pentyl or 2-(3-ethyl)-pentyl.

1-(4-lower alkyl)-piperazino is, for example, 4-methyl-, 4-ethyl-, 4-propyl-, 4-isopropyl- or 4-butyl-, 4-secondary butyl-, 4-isobutyl- or 4-tertiary butyl-piperazino, or 4-pentyl, 4-hexyl- or 4-heptyl-piperazino. Similarly, 1-(4-lower alkyl-4-oxido)-piperazino represents, for example, 4-methyl-, 4-ethyl-, 4-propyl-, 4-isopropyl- or 4-butyl-, 4-secondary butyl-, 4-isobutyl- or 4-tertiary butyl-4-oxido-piperazino, or 4-pentyl, 4-hexyl- or 4-heptyl-4-oxido-piperazino. 1-[4-(hydroxy-lower alkyl)]-piperazino in which the hydroxy group is bonded in a position higher than the α-position is, for example, 1-[4-(2-hydroxyethyl)]-piperazino or 1-[4-(3-hydroxypropyl)]-piperazino.

Lower alkylene is, for example, ethylene, 1,2- or 1,3-propylene or 1,2-, 1,3- or 1,4-butylene, or pentylene, hexylene or heptylene.

Phenyl-lower alkyl is, for example, benzyl, 1- or 2-phenylethyl or 1-, 2- or 3-phenylpropyl, or phenylbutyl.

Lower alkenyl is, for example, allyl or 2- or 3-butenyl.

Lower alkoxy is, for example, methoxy, ethoxy, propoxy, isopropoxy, butoxy, secondary butoxy, isobutoxy or tertiary butoxy, or pentyloxy, hexyloxy or heptyloxy. Similarly, lower alkoxycarbonyl represents, for example, methoxy-, ethoxy-, propoxy-, isopropoxy-, butoxy-, secondary butoxy-, isobutoxy- or tertiary butoxy-carbonyl, pentyloxy-, hexyloxy- or heptyloxy-carbonyl.

Lower alkanoyl is, for example, formyl, acetyl, propionyl, butyryl, isobutyryl, or pentanoyl, for example pivaloyl, hexanoyl or heptanoyl.

Di-lower alkylamino is, for example, dimethylamino or diethylamino. Similarly, di-lower alkylamino-lower alkylimino is, for example, dimethylaminomethylimino or diethylaminomethylimino, or especially dimethylaminoethylimino or 2-(diethylamino)-ethylimino.

Lower alkylimino is, for example, methylimino, ethylimino, propylimino, isopropylimino or butylimino.

Lower alkenylimino is, for example, allylimino.

Phenyl-lower alkylimino is, for example, benzyl- or 2-phenylethylimino.

Lower alkanoylimino is, for example, acetylimino, propionylimino, butyrylimino, isobutyrylimino or pivaloylimino.

Lower alkoxycarbonylimino is, for example, methoxy-, ethoxy-, propoxy-, isopropoxy-, butoxy- or tertiary butoxycarbonylimino.

Lower alkanesulphonylimino is, for example, methanesulphonylimino or ethanesulphonylimino.

Mono- or di-lower alkylcarbamoylimino is, for example, methyl-, ethyl- or dimethyl-carbamoylimino.

Alkylene- or 3-aza, 3-oxa, or 3-thia-alkylenecarbamoylimino having from 5 to 8 ring members is, for example, pyrrolidino-, piperidino-, morpholino-, thiomorpholino- or piperazino-, or 4-methylpiperazino-, 4-methyl-4-oxidopiperazino- or 4-(2-hydroxyethyl)-piperazino-carbonylimino.

Halogen is, for example, halogen having an atomic number of up to and including 35, such as chlorine, or fluorine or bromine.

Salts of compounds of the formula I are, for example, their pharmaceutically acceptable salts, such as acid addition salts or, in the case of acidic compounds, for example those in which $R_1$ represents an $R_2$—alk—$X_2$— radical and $R_2$ is carboxy, salts thereof with bases, and, in the case of compounds in which $R_1$ represents 4-substituted 1-piperazino, quaternary salts thereof. Acid addition salts are, for example, mineral acid salts, such as hydrohalic acid salts, for example hydrochlorides or hydrobromides, or sulphuric acid salts, for example hydrogen sulphates or sulphates, amidosulphonic acid salts, such as optionally N-substituted sulphamic acid salts, for example sulphamates or N-cyclohexylsulphamates, or organic sulphonates, for example methane-, ethane-, benzene- or p-toluenesulphonates, also carboxylic acid salts, such as lower alkanoates, for example acetates, or tartrates, malates, fumarates, maleates and the like. Salts with bases are, for example, metal salts, such as alkali metal salts, for example sodium or potassium salts, alkaline earth metal salts, for example calcium or magnesium salts, and aluminium, zinc or copper salts, but also ammonium salts with ammonia or organic amines, for example with triethylamine or ethanolamine, diethanolamine or triethanolamine. Quaternary salts are, for example, quaternary salts with lower alkyl halides or lower alkyl sulphonates, for example 4,4-dimethyl-, 4,4-diethyl- or 4-ethyl-4-methyl halides or sulphonates, such as metho- or ethosulphonates.

The invention relates, for example, to compounds of the formula I in which $R_1$ represents, on the one hand, 1-piperazino optionally substituted in the 4-position by lower alkyl, hydroxy-lower alkyl in which the hydroxy group is bonded in a position higher than the α-position, and/or oxido or, on the other hand, a radical of the formula $R_2$—alk—$X_2$— in which $R_2$ represents carboxy optionally esterified by a lower alkanol or represents hydroxymethyl, alk represents lower alkylene and $X_2$ represents thio or oxy, and in which $X_1$ represents thioxo or oxo, Ph represents 1,2-phenylene optionally substituted, as well as by the group $R_1$—C(=$X_1$)—NH—, by lower alkyl, lower alkoxy, lower alkanoyl, trifluoromethyl and/or halogen, $X_3$ represents oxy, thio, or imino optionally substituted by lower alkyl, di-lower alkylamino-lower alkyl, by phenyl or phenyl-lower alkyl each optionally substituted by lower alkyl, lower alkoxy and/or halogen, by lower alkenyl, lower alkanoyl, lower alkoxycarbonyl, lower alkanesulphonyl, mono- or di-lower alkylcarbamoyl or by alkylene- or 3-aza-, 3-oxa- or 3-thia-alkylenecarbamoyl each having from 5 to 8 ring members, and $R_3$ represents optionally fluorine-substituted lower alkyl or 3- to 8-membered cycloalkyl, and their salts, especially pharmaceutically acceptable salts.

The invention relates especially to compounds of the formula

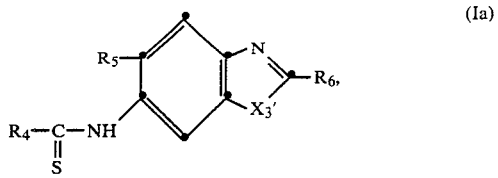

in which $R_4$ represents, on the one hand, 1-piperazino, 1-(4-lower alkyl)-piperazino having up to and including 4 C-atoms in the lower alkyl moiety, such as 1-(4-methyl)-piperazino, 1-(4-lower alkyl-4-oxido)-piperazino having up to and including 4 C-atoms in the lower alkyl moiety, such as 1-(4-methyl-4-oxido)-piperazino, or 1-[4-(hydroxy-lower alkyl)]-piperazino in which the hydroxy group is bonded in a position higher than the α-position and hydroxy-lower alkyl has up to and including 4 C-atoms, such as 1-[4-(2-hydroxyethyl)]-piperazino, or, on the other hand, a group of the formula $R_7$—alk'—$X_2$—, in which $R_7$ represents carboxy or lower alkoxycarbonyl having a total of up to and including 5 C-atoms, such as methoxycarbonyl or ethoxycarbonyl, or hydroxymethyl, alk' represents lower alkylene having up to and including 4 C-atoms, such as ethylene or 1,3-propylene, and $X_2$ represents oxygen or, preferably, sulphur, and in which $R_5$ represents hydrogen, lower alkyl having up to and including 4 C-atoms, such as methyl, lower alkoxy having up to and including 4 C-atoms, such as methoxy, or halogen having an atomic number of up to and including 35, such as chlorine, $X_3'$ represents oxy, thio, imino, lower alkylimino having up to and including 4 C-atoms, such as methylimino, lower alkanesulphonylimino having up to and including 4 C-atoms, such as methanesulphonylimino, lower alkoxycarbonylimino having up to and including 5 C-atoms, such as ethoxycarbonylimino, di-lower alkylcarbamoylimino having up to and including 8 C-atoms, such as dimethylcarbamoylimino, or phenyl-lower alkylimino having up to and including 10 C-atoms, such as benzylimino, and $R_6$ represents α-branched lower alkyl having up to and including 4 C-atoms or straight-chain lower alkyl having up to and including 4 C-atoms bonded by a secondary C-atom, such as tertiary butyl or isopropyl, and their salts, especially pharmaceutically acceptable salts.

The invention relates especially to compounds of the formula Ia in which $R_4$ represents, on the one hand, 1-(4-lower alkyl)-piperazino having up to and including 4 C-atoms in the lower alkyl moiety, such as 1-(4-methyl)-piperazino, 1-(4-lower alkyl-4-oxido)-piperazino having up to and including 4 C-atoms in the lower alkyl moiety, such as 1-(4-methyl-4-oxido)-piperazino, 1-[4-(hydroxy-lower alkyl)]-piperazino in which the hydroxy group is bonded in a position higher than the α-position and hydroxy-lower alkyl has up to and including 4 C-atoms, such as 1-[4-(2-hydroxyethyl)]-piperazino, or, on the other hand, a group of the formula $R_7$—alk'—$X_2$— in which $R_7$ represents carboxy or lower alkoxycarbonyl having a total of up to and including 5 C-atoms, such as methoxycarbonyl or ethoxycarbonyl, alk' represents lower alkylene having up to and including 4 C-atoms, such as ethylene or 1,3-propylene, and $X_2$ represents sulphur, and in which $R_5$ represents hydrogen, lower alkyl having up to and including 4 C-atoms, such as methyl, lower alkoxy having up to and including 4 C-atoms, such as methoxy, or halogen having an atomic number of up to and including 35, such as chlorine, $X_3'$ represents thio and $R_6$ represents α-branched lower alkyl having up to and including 4 C-atoms or straight-chain lower alkyl having up to and including 4 C-atoms bonded by a secondary C-atom, such as tertiary butyl or isopropyl, and their salts.

The invention relates first and foremost to compounds of the formula Ia in which $R_4$ represents, on the other hand, 1-(4-lower alkyl)-piprazino having up to and including 4 C-atoms in the lower alkyl moiety, such as 1-(4-methyl)-piperazino, or, on the other hand, ω-carboxy-lower alkylthio having up to and including 4 C-atoms in the lower alkyl moiety, such as 2-carboxyethylthio, and in which $R_5$ represents hydrogen, lower alkoxy or lower alkyl, each having up to and including 4 C-atoms, such as methoxy or methyl, $X_3'$ is thio and $R_6$ represents α-branched lower alkyl having up to and including 4 C-atoms, such as tertiary butyl, and their salts.

The invention relates especially to the compounds of the formula I mentioned in the Examples and their salts.

The compounds of the formula I can be manufactured according to methods known per se, for example by condensing with one another compounds of the formulae

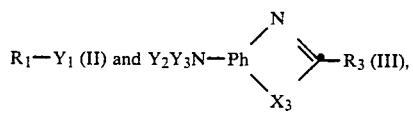

$R_1$—$Y_1$ (II) and $Y_2Y_3N$—Ph in which $Y_1$ represents hydrogen and $Y_2$ and $Y_3$ together represent a group of the formula =C=$X_1$, or one of the radicals $Y_1$ and $Y_2$ represents a group of the formula —C(=$X_1$)—$Y_4$, in which $Y_4$ represents a group that can be split off, and the other and $Y_3$ represent hydrogen, or, if $R_1$ represents a group of the formula $R_2$—alk—$X_2$—, $Y_1$ is cyano and $Y_2$ and $Y_3$ represent hydrogen, or condensing with one another salts thereof, and, if desired, converting a compound obtainable according to the invention into a different compound of the formula I and/or converting a free compound obtainable according to the invention into a salt or a salt obtainable according to the invention into the free compound or into a different salt.

The radical $Y_4$ which can be split off is, for example, optionally esterified or etherified hydroxy, optionally etherified mercapto or quaternary ammonio. Esterified hydroxy is, for example, hydroxy esterified by an organic carboxylic acid, such as lower alkanoyloxy, such as acetoxy, or a benzoyloxy group, but is preferably reactive esterified hydroxy, such as halogen, for example chlorine or bromine. Etherified hydroxy is, for example, lower alkoxy, or a benzyloxy or phenoxy group. Similarly, etherified mercapto is, for example, lower alkylthio or a benzylthio or phenylthio group. Quaternary ammonio is, for example, tri-lower alkylammonio, for example trimethylammonio or triethylammonio, or pyridinio. Using starting materials of the formula II in which $R_1$ represents a 1-piperazino radical optionally substituted in the 4-position, there comes into consideration as the radical that can be split off also primary, secondary or tertiary amino, for example amino, N-mono-lower or N,N-di-lower alkylamino, for example methylamino, ethylamino, dimethylamino or diethylamino, N,N-alkyleneamino, such as piperidino, pyrrolidino, morpholino, thiomorpholino or an anilino or diphenylamino group. Benzoyloxy, benzyloxy, phenoxy, phenylthio, pyridino, anilino and diphenylamino groups, and likewise the phenyl moiety of benzyloxy and benzylthio groups, may also be substituted, for example by lower alkyl, lower alkoxy, halogen and/or nitro.

Salts of starting materials of the formulae II and III are, for example, metal salts of compounds of the formula II in which $R_1$ represents a HOOC—alk—$X_2$ group, for example alkali metal or alkaline earth metal salts, for example the sodium or potassium salts, of the same, and also acid addition salts of compounds of the formula II in which $R_1$ represents 1-piperazino optionally substituted in the 4-position and $Y_1$ represents hydrogen, and of compounds of the formula III in which $Y_2$ represents a —C(=$X_1$)—$Y_4$ radical or hydrogen, $Y_3$ represents hydrogen and $Y_4$ represents reactive esterified hydroxy, for example mineral acid addition salts thereof, such as hydrohalides, for example hydrochlorides or hydrobromides, or sulphuric acid addition salts thereof, for example hydrogen sulphates.

The reaction is carried out in customary manner, especially in the manner known from the literature for analogous reactions, preferably in a solvent, for example a lower alkanol, if necessary in the presence of a condensing agent, in the case of the reaction of compounds of the formulae II and III in which one of the radicals $Y_1$ and $Y_2$ represents a —C(=$X_1$)—$Y_4$ group and $Y_4$ represents reactive esterified hydroxy preferably a basic condensing agent, in the case of the reaction of compounds of the formulae II and III in which one of the radicals $Y_1$ and $Y_2$ represents a —C(=$X_1$)—$Y_4$ group and $Y_4$ represents an optionally etherified mercapto group or an etherified hydroxy group, with, for example, the removal, by distillation or azeotropic distillation, of the split off hydrogen sulphide, mercaptan or alcohol, and/or at elevated temperature, for example at boiling temperature. Basic condensing agents are bases suitable for the formation of liberated hydrohalic acid, such as inorganic bases, for example sodium, potassium or calcium hydroxide, carbonate or bicarbonate, or organic nitrogen bases, for example triethylamine or pyridine.

Some of the starting materials of the formulae II and III are known. Novel compounds of the formulae II and III can be manufactured analogously to the manner in which the known starting materials are produced, and the present invention relates also to these novel compounds, to processes for their manufacture, and their use.

Compounds of the formulae II and III in which $Y_1$ and $Y_2$, respectively, represent a —C(=$X_1$)—$Y_4$ group, can be manufactured, for example, by reacting a compound of the formula II or III, in which $Y_1$ or $Y_2$, respectively, and/or $Y_3$ each represents hydrogen, in customary manner with a compound of the formula $Y_4'$—C(=$X_1$)—$Y_4'$ (IIa), in which each of the $Y_4'$ radicals, independently of one another, represents reactively esterified hydroxy, such as halogen, etherified hydroxy or etherified mercapto $Y_4$, for example with phosgene, thiophosgene, a haloformic acid ester, halothioformic acid ester or halodithioformic acid ester, or an N,N-di-substituted, such as N,N-di-lower alkylated, carbamoyl halide.

Compounds of the formula III in which $Y_2$ and $Y_3$ together represent a $=C=X_2$ group, can be obtained, for example, by reacting a compound of the formula III in which each of $Y_2$ and $Y_3$ represents hydrogen with a compound of the formula $Y_4'-C^3(=X_1)-Y_4'$ (IIa) in which each of the two radicals, $Y_4'$, independently of one another, represents reactively esterified hydroxy, etherified hydroxy or etherified mercapto, such as with phosgene, thiophosgene, a haloformic acid ester, halothioformic acid ester or halodithioformic acid ester, of a N,N-di-substituted, such as N,N-di-lower alkylated, carbamoyl halide, in the presence of a basic condensing agent, such as an inorganic base, pyridine or a tri-lower alkylamine, or a carbodiimide, with a tertiary amine and carbon disulphide, with an optionally substituted benzoyl isothiocyanate or with an alkali metal or ammonium thiocyanate, and in each case thermal decomposition of the resulting thiourea compound, or by reaction with hydrogen chloride and ammonium cyanate or ammonium thiocyanate. By such reactions chiefly the compounds of the formula III mentioned as starting materials in which $Y_2$ represents a $-C(=X_1)-Y_4$ group are formed, and these can be recovered either by reaction with a compound of the formula II in which $Y_1$ is hydrogen, or, in the absence of such a compound, can be further reacted to form isocyanates or isothiocyanates of the formula III. Starting materials of the formula III in which $Y_2$ represents a $-C(=X_1)-Y_4$ group and $Y_3$ represents hydrogen are accordingly preferably formed in situ under the reaction conditions to be used for their further processing and are further reacted without isolation.

The compounds of the formula I can furthermore be produced by converting $Y_5$ in a compound of the formula IV

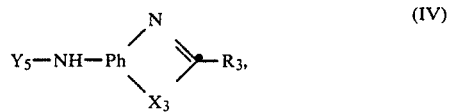

in which $Y_5$ represents a radical that can be converted into a group of the formula $R_1-C(=X_1)-$, or in a salt thereof, into a group of the formula $R_1-C(=X_1)-$, and, if desired, converting a compound obtainable according to the invention into a different compound of the formula I and/or converting a free compound obtainable according to the invention into a salt or a salt obtainable according to the invention into the free compound or into a different salt.

Radicals that can be converted into a group of the formula $R_1-C(=X_1)-$ are, for example, those that can be converted into a group of the formula $R_1-C(=X_1)-$ by solvolysis, i.e. reaction with water (hydrolysis), hydrogen sulphide or one of its salts or an alcohol (alcoholysis) or by reduction or oxidation.

Salts of compounds of the formula IV are, for example, acid addition salts, such as hydrochlorides, or sulphonic acid salts.

Radicals that can be converted into groups of the formula $R_1-C(=X_1)-$ by solvolysis are, for example, those of the formulae $Y_6-C(=X_1)-$, $R_1-C(Y_7Y_8)-$ or $Y_6-C(Y_7Y_8)-$ in which $Y_7$ and $Y_8$, independently of one another, represent esterified hydroxy groups or hydroxy groups etherified by a monohydric alcohol, or mercapto groups etherified by a monovalent mercaptan, or together represent hydroxy groups etherified by a dihydric alcohol or mercapto groups etherified by a divalent mercaptan, or an imino group optionally present in salt form, and $Y_6$ represents a 1-piperazino group substituted in the 4-position by a radical that can be split off by solvolysis, or a $Y_9-alk-X_2-$ group in which $Y_9$ represents an esterified hydroxymethyl group, a hydroxymethyl group etherified by a silanol or a cyclic 2-hydroxyether or 2- or 4-hydroxy ether, or esterified by a carboxylic acid, or represents functionally modified carboxy of the formula $-C(=O)-Y_6$ other than esterified carboxy.

Esterified hydroxy is, for example, hydroxy esterified by a hydrohalic acid or by an organic carboxylic acid, such as halogen, for example chlorine or bromine, lower alkanoyloxy, for example acetoxy or pivaloyloxy, or optionally substituted benzoyloxy. Hydroxy etherified by a monohydric alcohol is, for example, lower alkoxy, for example methoxy or ethoxy. Likewise, mercapto etherified by a monovalent mercaptan is, for example, lower alkylthio, for example methylthio or ethylthio. Hydroxy groups etherified by a dihydric alcohol are, for example, lower alkylenedioxy, for example ethylenedioxy or propylenedioxy, and mercapto groups etherified by a divalent mercaptan are, for example, lower alkylenedithio, for example ethylenedithio or propylenedithio.

An imino group optionally present in salt form is, for example, imino optionally present as a hydrohalide, such as a hydrochloride or hydrobromide, a sulphonic acid salt, for example methanesulphonate or p-toluenesulphonate, or a sulphuric acid mono-ester salt, for example methosulphate. Radicals in the 4-position of a piperazino group that can be split off by solvolysis are, for example, the acyl radicals derived from an organic carboxylic acid or a semi-ester or monohalide of carbonic acid, such as lower alkanoyl, for example acetyl, or optionally substituted benzoyl, lower alkoxycarbonyl groups or optionally substituted benzyloxycarbonyl or phenyloxycarbonyl groups or halogencarbonyl.

Hydroxymethyl groups etherified by a silanol are, for example, tri-lower alkylsilyloxymethyl groups, such as trimethylsilyloxymethyl. Hydroxy etherified by a cyclic 2-hydroxyether is, for example, 2-tetrahydropyranyloxymethyl, and by a cyclic 2- or 4-hydroxythioether, for example 2-tetrahydrothiopyranyloxymethyl or 4-dihydrothiopyranyloxymethyl.

Hydroxymethyl esterified by a carboxylic acid is, for example, hydroxymethyl esterified by an organic carboxylic acid or a semi-ester or monohalide of carbonic acid, such as lower alkanoyloxymethyl, for example acetoxymethyl, optionally substituted benzoyloxymethyl, lower alkoxycarbonyloxymethyl, optionally substituted benzyloxy- or phenoxy-carbonyloxymethyl, or chlorocarbonyloxymethyl. Functionally modified carboxy groups $-C(=O)-Y_6$ other than esterified carboxy are preferably cyano, iminoether or iminoester groupings optionally present in salt form, for example as hydrohalide, methanesulphonate, p-toluenesulphonate or methosulphate, or orthoester or orthoanhydride groupings, such as tri-lower alkoxymethyl or trihalomethyl, for example trichloromethyl, and amidated or anhydridised carboxy, such as optionally substituted carbamoyl or halocarbonyl.

By hydrolysis of the mentioned groups, for example starting from radicals $Y_5$ of the formulae $Y_6$—C($Y_7Y_8$)—, $R_1$—C($Y_7Y_8$)— and $Y_6$—C(=O)— groups of the formula $R_1$—C(=O) or starting from radicals of the formula $Y_6$—C(=S)— or $Y_6$—C($Y_7Y_8$), in which $Y_7$ and $Y_8$ represent etherified mercapto, groups of the formula $R_1$—C(=S)— are obtained, in which $R_1$ represents 4-unsubstituted 1-piperazino or a $R_2$-alk-$X_2$ group and $R_2$ is carboxy or hydroxymethyl, and starting from $Y_6$—C(=$X_1$)— groups, in which $Y_6$ represents a $Y_9$—alk—$X_2$— group and $Y_9$ represents an iminoether or orthoester group, groups of the formula $R_1$—C(=$X_1$)— are obtained in which $R_1$ is a $R_2$—alk—$X_2$— group and $R_2$ is esterified carboxy.

The hydrolysis is carried out in customary manner, for example in the presence of a hydrolysing agent, if necessary in a water-miscible organic solvent, at elevated or reduced temperature, for example in a temperature range of from approximately 0° to 120° C., and/or under inert gas, such as nitrogen. There come into consideration as hydrolysing agents, for example acidic hydrolysing agents, and in the case of starting compounds of the formula IV in which $Y_5$ has a 1-piperazino radical substituted in the 4-position by a group that can be split off by hydrolysis, or a hydroxymethyl group esterified by a carboxylic acid or a functionally modified carboxy group $Y_9$, also basic hydrolysing agents. Acid hydrolysing agents are, for example, mineral acids, such as hydrohalic acids, for example hydrochloric acid, or acid salts thereof, for example ammonium chloride, or sulphuric acid or hydrogen sulphates, and also organic carboxylic acids, such as lower alkanoic acids, for example acetic acid. Basic hydrolysing agents are, for example, hydroxides or carbonates of alkali metals or alkaline earth metals, for example sodium, potassium or calcium hydroxide, sodium carbonate or potassium carbonate. Water-miscible organic solvents are, for example, alcohols, such as lower alkanols, for example methanol or ethanol, di-lower alkyl ketones, for example acetone, cyclic ethers, such as dioxan or tetrahydrofuran, dimethylformamide or dimethyl sulphoxide.

By reaction with hydrogen sulphide or one of its salts, such as a metal or ammonium sulphide, for example potassium, sodium or ammonium sulphide, for example groups of the formula $R_1$—C($Y_7Y_8$)— can be converted into groups of the formula $R_1$—C(=S)—.

The reaction with hydrogen sulphide or one of its salts is carried out in customary manner, for example in a solvent and, if necessary, in the presence of a customary catalysis or condensation agent, while cooling or heating, for example in a temperature range of from approximately 0° to 120° C., and/or under inert gas, such as nitrogen. Suitable solvents are, for example, polar solvents, such as water, alcohols, for example methanol or ethanol, cyclic ethers, such as tetrahydrofuran, dimethylformamide or dimethyl sulphoxide or mixtures thereof.

By alcoholysis, for example groups of the formula $Y_6$—C(=$X_1$)—, in which $Y_6$ represents a $Y_9$—alk—$X_2$— group and $Y_9$ represents anhydridised carboxy, or hydroxymethyl esterified by an organic carboxylic acid, can be converted into groups of the formula $R_2$—alk—$X_2$—, in which $R_2$ is esterified carboxy, or hydroxymethyl.

The alcoholysis is carried out in customary manner, for example in the presence of an acidic or basic agent and, if necessary, in a solvent, while cooling or heating, for example in a temperature range of from approximately 0° to 120° C., and/or under inert gas. Acidic agents are, for example, mineral acids, such as hydrohalic acids, for example hydrogen chloride or bromide, or sulphuric acid. Basic agents are, for example, alkali metal hydroxides, for example sodium or potassium hydroxide, or alkali metal alcoholates, such as the sodium or potassium alcoholate of the alcohol used. Solvents are, for example, solvents miscible with the alcohol to be used, or alternatively an excess of the same.

Radicals $Y_5$ that can be converted into groups of the formula $R_1$—C(=$X_2$)— by reduction are, for example, those of the formula $Y_{10}$—C(=$X_1$)—, in which $Y_{10}$ represents an O=HC—alk—$X_2$— group or a 1-piperazino radical substituted in the 4-position by α-aralkyl- or α-aralkoxycarbonyl, such as benzyl or benzyloxycarbonyl. These radicals can be reduced to radicals of the formula $R_1$—C(=$X_1$)—, in which $R_1$ represents a group of the formula $HOCH_2$—alk—$X_2$— or a 4-unsubstituted 1-piperazino radical.

The reduction is carried out in customary manner, starting from compounds of the formula IV in which $Y_5$ represents a group of the formula O=CH—alk—$X_2$—C(=$X_1$)—, by treating with an alcohol, for example with an alkanol or cycloalkanol, such as isopropanol or cyclohexanol, in the presence of an appropriate aluminium alcoholate, or by reaction with an alkali metal borohydride, such as sodium borohydride or sodium cyanoborohydride, or with formic acid, and, starting from compounds of the formula IV in which $Y_1$ represents a $Y_{10}$—C(=$X_1$)— group and $Y_{10}$ represents piperazino substituted by α-aralkyl- or α-aralkoxycarbonyl, by treatment with catalytically activated hydrogen, such as hydrogen in the presence of a hydrogenation catalyst, for example a palladium, nickel or platinum catalyst, inter alia palladium-on-carbon or Raney nickel. The process is carried out in customary manner, for example in an inert solvent, such as an alcohol, for example an excess of the alcohol used as reducing agent, or a lower alkanol, if necessary while cooling or heating, for example in a temperature range of from approximately $-10°$ to 100°—when treating with hydrogen if necessary under elevated pressure, for example in a pressure range of from approximately 1 up to 20 bar—and, if necessary, in a closed vessel and/or under inert gas.

By oxidation, for example a group $Y_5$ of the formula O=CH—alk—$X_2$—C(=$X_1$)— can be converted into a group $R_1$ of the formula HOOC—alk—$X_2$—C(=$X_1$)—. There come into consideration as oxidising agents, for example oxidising heavy metal compounds, such as chromium(VI), manganese(IV) and manganese(VII) compounds, for example chromium trioxide, chromic acid or chromic acid salts, manganese dioxide or potassium permanganate, and also oxygen, if necessary in the presence of a solvent, for example water, a carboxylic acid, such as acetic acid, a ketone, such as acetone, or in the presence of mixtures, including aqueous mixtures, thereof, while cooling or heating, for example in a temperature range of from approximately $-20°$ to $+100°$ C., in a closed vessel and/or under inert gas, such as nitrogen.

In the above-mentioned reduction and oxidation processes, the formyl group in a compound of the formula IV in which $Y_5$ represents a O=HC—alk—$X_2$—C(=$X$-

1)— group may also be formed in situ, for example by oxidation of an optionally esterified hydroxymethyl group, such as a hydroxymethyl group optionally esterified by a hydrohalic acid or a carboxylic acid, for example from hydroxymethyl, chloro- or bromomethyl, lower alkanoyloxymethyl or lower alkoxycarbonyloxymethyl, or may be freed, for example by hydrolysis, from a functionally modified formyl group, such as an acetalised, thioacetalised or acylalised formyl group, for example di-lower alkoxy- or lower alkylenedioxymethyl, di-lower alkylthio- or lower alkylenedithiomethyl, dichloromethyl or di-lower alkanoyloxymethyl, or from an optionally substituted iminomethyl group, for example iminomethyl or anilinomethyl.

Novel starting materials of the formula IV can be produced in an analogous manner to that for the production of the known starting materials.

Thus, compounds of the formula IV in which $Y_5$ represents a group of the formula $Y_6$—C(=$X_1$)— or $Y_{10}$—C(=$X_1$)— are obtained, for example, by reacting a compound of the formula $Y_6$—H (IVa) or $Y_{10}$—H (IVb), respectively, with a compound of the formula

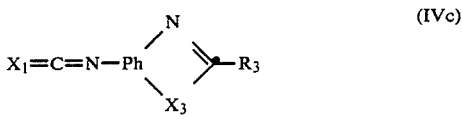
(IVc)

or by reacting a compound of the formula $Y_6$—C(=$X_1$)—Hal (IVd) or $Y_{10}$—C(=$X_1$)—Hal (IVe), respectively, in which Hal is halogen, such as chlorine, with a compound of the formula

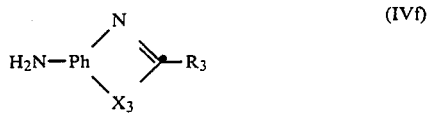
(IVf)

preferably in the manner indicated for the reaction of compounds of the formulae II and III.

Compounds of the formula IV in which $Y_5$ represents a $R_1$—C($Y_7Y_8$)— or $Y_6$—C($Y_7Y_8$)— group are obtained, for example, by condensing a compound of the formula IVd, or IVe, respectively, in customary manner, first with an orthoformic acid derivative of the formula H—C($Y_7Y_7Y_8$) IVg and then with a compound of the formula IVf.

The compounds of the formula I can furthermore be produced by cyclising a compound of the formula V

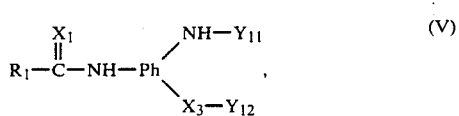
(V)

in which one of the radicals $Y_{11}$ and $Y_{12}$ represents a group of the formula —C(=$Y_{13}$)—$R_3$ and the other represents a radical that can be split off and $Y_{13}$ represents optionally functionally modified oxo, or a salt thereof, and, if desired, converting a compound obtainable according to the invention into a different compound of the formula I and/or converting a free compound obtainable according to the invention into a salt or a salt obtainable according to the invention into the free compound or into a different salt.

Radicals that can be split off are, for example, groups of the formula —C(=$Y_{13}$)—$R_3$, hydrogen, acyl, or sulpho, optionally present in salt form, bonded to thio $X_3$. Acyl in that case is especially acyl of the formula $R_3$—C(=O)—. Functionally modified oxo is, for example, thioxo or imino.

Salts of compounds of the formula V are, for example, acid addition salts thereof, such as hydrohalides, for example hydrochlorides, or alkali metal salts of compounds of the formula V in which —$X_3$—$Y_{12}$ is sulpho, hydroxy or mercapto, such as sodium or potassium salts thereof.

The cyclisation is carried out in customary manner, if necessary in the presence of a condensing agent and/or a solvent, if necessary while cooling or heating, for example in a temperature range of from approximately 0° to 130° C., in a closed vessel and/or under inert gas, such as nitrogen. Condensing agents are, for example, acidic or basic condensing agents. Acidic condensing agents, the use of which is indicated especially when using compounds of the formula V in which $Y_{12}$ represents acyl as starting materials, are, for example, mineral acids or their acid salts and acid anhydrides, such as hydrohalic acid, for example hydrogen chloride, sulphuric acid or hydrogen sulphates, for example potassium or ammonium hydrogen sulphate, phosphoric acid or its acid anhydrides, such as polyphosphoric acid or boric acid, also sulphonic acids, such as p-toluenesulphonic acid, or Lewis acids, such as boron trifluoride or antimony pentachloride. Instead of carrying out the cyclisation in the presence of an acidic condensing agent, the compound to be cyclised can alternatively be used in the form of an acid addition salt. Basic condensing agents are, for example, alkali metal or alkaline earth metal hydroxides, such as sodium, potassium or calcium hydroxide, alkali metal carbonates, for example sodium or potassium carbonate, or organic nitrogen bases, preferably tertiary amines, such as pyridine or tri-lower alkylamines, for example triethylamine. Instead of carrying out the cyclisation in the presence of a base, a compound of the formula V in which —$X_3$—$Y_{12}$ represents hydroxy or mercapto can alternatively be used in the form of an alkali metal salt. Suitable solvents are, for example, aromatic or araliphatic hydrocarbons, for example benzene, toluene, xylenes, halohydrocarbons, for example di-, tri- and tetrachloromethane, aliphatic or cyclic ethers, for example diethyl ether, dioxan, tetrahydrofuran, dimethylformamide or dimethyl sulphoxide, also water and aqueous solvents of the type mentioned.

Novel starting materials of the formula V can be produced in a manner analogous to that used for known starting materials.

Thus, compounds of the formula V in which $Y_{11}$ represents a group of the formula —C(=$Y_{13}$)—$R_3$ and $Y_{12}$ represents hydrogen or likewise a group of the formula —C(=$Y_{13}$)—$R_3$, are obtained, for example, by reacting a compound of the formula Va $$\begin{array}{c} X_1 \\ \parallel \\ R_1-C-NH-Ph \end{array} \begin{array}{c} NH_2 \\ \diagup \\ \diagdown \\ X_3H \end{array} \quad (Va)$$

with a compound of the formula Z—C(=$Y_{13}$)—$R_3$ (Vb), in which Z represents hydroxy and $Y_{13}$ represents oxo, or Z represents etherified hydroxy and $Y_{13}$ represents oxo or imino, or Z represents reactive esterified hydroxy, for example halogen, and $Y_{13}$ represents oxo, thioxo or imino, or Z represents a group of the formula —O—C(=O)—R$_3$ and Y$_{13}$ *l represents oxo, or Z and Y*$_{13}$ together represent nitrilo, or with a salt thereof, for example an iminium hydrohalide of a compound of the formula Vb in which Y$_{13}$ is imino. The reaction is carried out in the usual manner, in the case of the reaction with compounds of the formula Vb in which Z represents reactive esterified hydroxy or a —O—C(=Y$_{13}$)—R$_3$ group in the presence of a basic condensing agent, in the case of the reaction with compounds of the formula Vb in which Z and Y$_{13}$ together represent nitrilo in the presence of an acidic condensing agent, and in the case of the reaction with compounds of the formula Vb in which Z represents hydroxy and Y$_{13}$ represents oxo in the presence of a water-binding agent. Basic condensing agents are, for example, alkali metal and alkaline earth metal hydroxides, for example sodium, potassium or calcium hydroxide, alkali metal carbonates, for example sodium or potassium carbonate, alkali metal, alkaline earth metal and ammonium salts of acids of the formula HO—C(=O)—R$_3$, such as their sodium, potassium, ammonium or magnesium salts, or tertiary organic nitrogen bases, such as pyridine or tri-lower alkylamines, such as triethylamine. Acidic condensing agents are, for example, hydrohalic acids, such as hydrogen chloride or hydrogen bromide. Water-binding agents are, for example, carbodiimides, such as dicyclohexylcarbodiimide.

The compounds of the formula Va used as starting materials can be obtained, for example, by reducing the nitro groups and optionally the disulphide bridge in a corresponding nitro compound (containing nitro instead of —NH$_2$) or a disulphide (containing the group —S—S—Ph(NO$_2$)—NH—C(=X$_1$)—R$_1$ instead of —X$_3$H), for example by reaction with hydrogen in the presence of a hydrogenation catalyst for example palladium-on-carbon, with reducing metals or metal compounds, for example iron, zinc, tin or tin(II) chloride or, to reduce a disulphide bridge, with sodium borohydride or, to reduce nitro, with sulphonated sodium borohydride.

Compounds of the formula V in which Y$_{11}$ represents hydrogen and Y$_{12}$ represents a —C(=Y$_{13}$)—R$_3$ group can be produced, for example, by reacting a compound of the formula

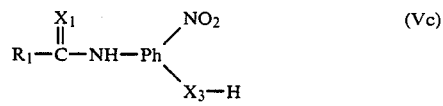

(Vc)

with a compound of the formula Z—C(=Y$_{13}$)—R$_3$ (Vb) in which Z represents hydroxy and Y$_{13}$ represents oxo, or Z represents etherified hydroxy and Y$_{13}$ represents oxo or imino, or Z represents reactive esterified hydroxy, for example halogen, and Y$_{13}$ represents oxo, thioxo or imino, or Z represents a group of the formula —O—C(=O)—R$_3$ and Y$_{13}$ represents oxo, or Z and Y$_{13}$ together represent nitrilo, or with a salt, for example an iminium hydrohalide of a compound of the formula Vb in which Y$_{13}$ is imino, and reducing the nitro group, for example by means of sulphonated sodium borohydride or reducing metals or metal compounds, for example iron, zinc, tin or tin(II) chloride. The reaction with compounds of the formula Vb is carried out under the conditions given above.

The compounds of the formula Vc used as starting materials therefor can be produced, for example, by protecting the X$_3$H group in a compound of the formula

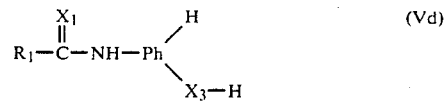

(Vd)

for example by benzylation, benzoxycarbonylation or oxidation of a mercapto compound (X$_3$H=SH) to the disulphide, then nitrating and subsequently freeing the —X$_3$H group, for example by reduction.

Compounds of the formula V in which Y$_{11}$ represents a group of the formula —C(=Y$_{13}$)—R$_3$, X$_3$ represents thio and Y$_{12}$ represents sulpho optionally present in salt form, can further be produced by converting a compound of the formula

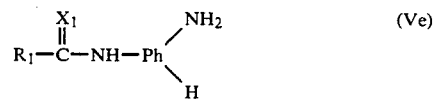

(Ve)

in customary manner by reaction with a thiosulphate, for example with sodium thiosulphate, into the Bunte salt (formula V; Y$_{11}$=H; —X$_3$—Y$_{12}$=—S—SO$_3^\ominus$) and further reacting this in the manner indicated with a compound of the formula Vb.

Compounds obtainable according to the invention can be converted into different compounds of the formula I.

For example, in a compound of the formula I in which R$_1$ represents a R$_2$—alk—X$_2$— group and R$_2$ represents esterified carboxy, the latter can be hydrolysed in customary manner to carboxy, for example in the presence of an acidic or basic condensing agent, if necessary in the presence of a solvent, while cooling or heating, for example in a temperature range of from approximately 0° to 120° C., and/or under inert gas, such as nitrogen. Acidic hydrolysing agents are, for example, protonic acids, such as mineral acids, for example hydrochloric or hydrobromic acid, sulphuric acid or phosphoric acid, organic sulphonic acids, for example p-toluenesulphonic acid, or organic carboxylic acids, for example acetic acid, and other lower alkanoic acids. Basic hydrolysing agents are, for example, metal or ammonium hydroxides, such as alkali metal or alkaline earth metal or ammonium hydroxides, for example sodium, potassium, calcium or ammonium hydroxide, or alkali metal carbonates, for example potassium or sodium carbonate, also organic bases, such as tertiary amines, for example triethylamine. Solvents are especially water-miscible solvents, such as lower alkanols, for example methanol or ethanol, water-miscible ethers or ketones, for example dioxan, tetrahydrofuran or acetone, dimethylformamide or dimethyl sulphoxide.

Furthermore, hydroxymethyl groups R$_2$ can be oxidised to carboxy groups. The oxidation can be carried out in a manner known per se, for example by reaction with an oxidising heavy metal compound, starting from hydroxymethyl preferably with a chromium(VI)- or manganese(VII)-containing oxidising compound, for example chromium trioxide or especially potassium permanganate, or with a manganese(IV)-containing compound, such as manganese dioxide. The oxidation is preferably carried out in the presence of a suitable solvent or diluent, for example acetone or pyridine, or a mixture, preferably an aqueous mixture, thereof, if necessary while cooling or heating, for example in a temperature range of from approximately 0° C. to approximately 80° C.

Also, resulting compounds in which $X_3$ is unsubstituted imino and/or $R_1$ is 4-unsubstituted piperazino, can be substituted at the imino group $X_3$ and/or in the 4-position of the piperazino group $R_1$. For example, imino $X_3$ can be N-oxidised by treating with a suitable N-oxidising agent, alkylated or phenylalkylated by reacting with a reactive ester of a lower alkanol or phenyl-lower alkanol, respectively, optionally substituted as indicated, or substituted, by reacting with a lower alkanoic acid anhydride or chloride or a halocarbonic acid lower alkyl ester, by a lower alkyl, phenyl-lower alkyl, lower alkanoyl or lower alkoxycarbonyl radical. Piperazino unsubstituted in the 4-position can be N-lower alkylated, for example, by reacting with a reactive ester of a lower alkanol, and piperazino optionally lower alkylated in the 4-position can be N-oxidised, for example, by treating with an N-oxidising agent.

Reactive esters for the above are especially mineral acid esters, such as hydrochloric, hydrobromic or hydriodic acid esters or sulphuric acid esters, and also esters with sulphonic acids, such as with fluorosulphonic acid or organic sulphonic acids, for example p-toluenesulphonates. The reaction with such reactive esters, and with acid anhydrides or chlorides, is carried out in customary manner, for example in the presence of a basic condensing agent, such as an alkali metal hydroxide or carbonate, for example sodium or potassium hydroxide or sodium or potassium carbonate, an alcoholate, for example an alkali metal lower alkoxide, such as sodium methoxide, or sodium hydride, advantageously in an inert solvent, for example in dimethylformamide or N-methylpyrrolidone.

Suitable N-oxidising agents are, for example, peroxy compounds, such as hydrogen peroxide, organic hydroperoxides, for example tert.-butyl hydroperoxide, organic peracids, such as aromatic or aliphatic percarboxylic acids, for example m-chloroperbenzoic acid, peroxyacetic acid or monoperphthalic acid, oxidising heavy metal compounds, such as chromium(VI) or manganese(IV) or manganese(VII) compounds, for example chromium trioxide, chromic acid, manganese dioxide or potassium permanganate, oxidising inorganic oxyacids, such as oxyacids of nitrogen, of the halogens, or chalcogens, or their anhydrides or salts, for example nitric acid, di-nitrogen tetroxide, selenium dioxide or sodium metaperiodate, and also ozone. Suitable solvents are, for example, halogenated hydrocarbons, such as haloalkanes, for example carbon tetrachloride, chloroform or methylene chloride, or carboxylic acids, such as alkanoic acids, for example acetic acid, or their anhydrides.

In a preferred embodiment of this oxidising process, for example compounds of the formula I in which $X_3$ represents imino or $R_1$ represents 1-piperazino optionally lower alkylated in the 4-position and one of the radicals $R_1$ and/or $X_3$ has an unsubstituted ring nitrogen atom can be N-oxidised by reaction with an organic peracid, for example with m-chloroperbenzoic acid, in a haloalkane, for example in chloroform.

Conversely, in compounds of the formula I in which $X_3$ represents N-oxidised imino and/or $R_1$ represents N-oxidised 1-piperazino optionally substituted by lower alkyl, the N-oxidised ring nitrogen atom(s) can be reduced. The reduction is carried out by treating with customary reducing agents, for example nascent or catalytically activated hydrogen, such as iron or zinc and acid, such as hydrochloric acid, or hydrogen in the presence of Raney nickel, advantageously in an inert solvent, such as a lower alkanol, or with a phosphorus-(III) compound, such as a phosphine, for example triphenylphosphine or tri-n-butylphosphine, or a phosphorous acid ester, such as a tri-lower alkyl phosphite, for example trimethyl or triethyl phosphite.

Resulting free salt-forming compounds of the formula I can be converted into salts in a manner known per se. Acids, for example, can be converted with a base or with a suitable salt of a carboxylic acid and bases with a mineral acid, usually in the presence of a solvent or diluent.

Resulting salts can be converted into the free compounds in a manner known per se, for example by treating with an acidic reagent, such as a mineral acid.

The compounds, including their salts, can also be obtained in the form of their hydrates, or incorporate the solvent used for crystallisation.

Owing to the close relationship between the novel compounds in free form and in the form of their salts, hereinbefore and hereinafter by free compounds there shall be understood, where appropriate and applicable, optionally also the corresponding salts, and vice versa.

The invention relates also to those embodiments of the process in which a compound obtainable at any stage of the process as intermediate is used as starting material and the remaining process steps are carried out, or in which a starting material is formed under the reaction conditions or is used in the form of a derivative, optionally a salt.

The starting materials used in the process of the present invention are preferably those that lead to the compounds described at the beginning as being especially valuable. The present invention relates also to novel starting materials and processes for their manufacture.

The novel compounds having a valuable antiparasitic action, especially against parasitic helminths. They exhibit, with very good tolerability, for example in test animals such as the mouse, dormouse (*Saccostomus campestris*), rat, golden hamster, Mongolian gerbil (*Meriones unguiculatus*), dog, monkey or hen, action against trematodes, such as fasciolidae, for example *Fasciola hepatica*, and especially schistosomes, for example *Schistosoma mansoni*, *Schistosoma japonicum* and *Schistosoma haematobium*, and against the pathogens of filariasis, for example *Dipetalonema viteae* and *Litomosoides carinii*. For example, the compounds of the present invention, in the treatment of golden hamsters with a 6 to 8 week old infection of *Schistosoma mansoni*, on administration once p.o. (for example, by a feeding tube), exhibit an $ED_{50}$ from approximately 30–200 mg/kg. Likewise, in the treatment of filariasis in the Mongolian gerbil (*Meriones unguiculatus*), the new compounds have proved to be macro- and microfilaricidal, that is to say on administration five times p.o. of a dosage from approximately 10–50 mg/kg both in the case of infections by *Dipetalonema viteae* and by *Litomosoides carinii*. The novel compounds can accordingly be used for the treatment of warm-blooded animals infected by parasitic helminths, such as those mentioned above, especially for the treatment of filariasis.

By means of the following test procedure, for example the anti-schistosomal activity of compounds of the formula I can be determined in the example of the white mouse and the Syrian hamster.

Adult white mice weighing from 20 to 25 g are infected by subcutaneous injection of 80 cercariae of *Schistosoma mansoni* per animal. These cercariae are all obtained from the same group of "positive" snails (species *Biomphilaria glabrata*) and groups each of 100 and 150 mice are injected. The Syrian hamsters are treated in the same manner.

Subsequently, the appearance of adult parasites is positively determined by the "miracidia hatching test". The test animals are divided at random into groups of 10 each, 2 groups being used as control groups. The remaining groups are treated with at least 3 differently graded individual doses of the test compounds. At the same time the animals of one control group are killed and autopsied to ascertain the average number of worms at the beginning of the observation phase.

14 days after treatment, the number of deposited viable eggs ascertained by means of the "miracidia hatching test" is recorded weekly. 6 weeks after treatment all the animals, including those of the untreated control groups, are killed and autopsied. The total number of schistosomes found is determined from each animal. The ratio of the average number of worms per treated group to the mean value of the two control groups is determined and the $ED_{50}$ value (50% reduction in comparison with the control values) is ascertained according to the L. C. Miller and M. L. Tainter method (Proc. Soc. Exp. Biol. Med. 57, 261–264, 1944).

To ascertain the antifilarial action of compounds of the formula I, the procedure is as follows, using as test animals Meriones (*Meriones unguiculatus*) and multimammate rats (*Mastomys natalensis*):

Young adult Meriones and multimammate rats from random breeds each weighing from 30 to 50 g are infected by tick bites of the species *Bdellonyssus bacoti* according to the F. Hawking and P. Swell method (Brit. J. Pharmacol. 3, 285–296, 1948). The infection containers are held in a state of continuous flux: each Monday, for example, the ticks are infected by *Litomosoides carinii*, which are in the larval stage, the mites being able to feed for 8 hours on the peripheral blood of different rodents which contains numerous microfilariae. On Thursdays, uninfected rodents are kept in the containers for 8 hours, during which they are bitten by freshly hatched, but chiefly older, ticks, containing metacyclic larvae ($L_3$) of the parasitic threadworms. The population density is held at a level of a minimum of 50 and a maximum of 200 microfilariae. After 9–10 weeks adult parasites are detected by the examination of 5 $mm^3$ blood samples from the capillary blood vessel system in which microfilariae circulate. The blood samples, to which heparin is added, are examined microscopically at a magnification of 100 and the number of living microfilariae are ascertained in 15 fields of 1.8 mm diameter. Only those animals containing more than 50 microfilariae are selected for further experiments. These animals are divided at random into different groups and kept individually in Macrolon ® cages. Groups of 3 animals each are treated with the test substances with differently dosed oral samples on 5 successive days. One group is used as an untreated control group.

On the same day after the treatment, the microfilariae are counted in exactly the same manner as before the treatment. These counts are carried out periodically 2, 4 and 6 weeks after the treatment, the total number of living and dead microfilariae in each animal being ascertained.

The minimum effective dosage (MED) against microfilariae is that dosage which, 5 days after treatment, leads to at least a 95% reduction of the number of microfilariae in the circulating blood. This dosage is usually verified in a second series of tests. As minimum curative dosage (MCD) against microfilariae, that dosage is taken which destroys all microfilariae in all of the treated animals during the six-week observation after treatment (H. P. Striebel, An. N. Y. Acad. Sci. 160, 491–498, 1978). For some slow-acting substances the period is extended to 8 weeks. Parallel to the repetition of the experiments for determining the MED, the MCD is likewise ascertained in a second series of tests.

A further test parasite is, inter alia, *Dipetalonema viteae*, which is kept in the same types of rodent as *Litomosoides carinii*. White ticks (*Ornithodorus moubata*) serve as intermediate hosts and after the infecting blood feed are kept at a temperature of 28° C. and a relative humidity of 70–80% up to approximately 7 weeks. Infected larvae are collected by immersing the ticks in a few drops of Hank's solution on petri dishes. The ticks are separated from the infected larvae in a Baerman apparatus in the same medium.

*M. natalensis* and *M. unguiculatus* are then infected by 70 larvae per animal by subcutaneous injection in the neck. 11 to 13 weeks after infection the animals are examined for microfilariasis as in the case of *L. carinii*. Only animals that have at least 50 microfilariae per 10 $mm^3$ of blood are used for the experiments. To minimise as far as possible the risk of "therapeutic shock", no animal is used that has been infected for longer than 13 weeks.

After evaluating this and further tests, compounds of the formula I prove to be excellent micro- and macrofilaricides, for example for lymphatic filariases and onchocercosis, and schistosomacides, for which an effective dosage range of approximately 3 to 80 mg/kg daily by oral administration over a period of 5 days is to be used.

The pharmaceutical preparations according to the invention, which contain compounds of the formula I or pharmaceutically acceptable salts thereof, are those for enteral, such as oral or rectal, and parenteral, administration to warm-blooded animals, that contain the pharmacological active substance alone or together with a pharmaceutically acceptable carrier. The dosage of the active substance depends on the species of warm-blooded animal, the age and the individual condition, and on the method of administration.

Normally, where administration is oral and the warm-blooded animal weighs approximately 75 kg, an approximate daily dosage of 0.25 to 2.5 g, advantageously divided into several equal portions, is estimated.

The new pharmaceutical preparations contain, for example, from approximately 10% to approximately 80%, preferably from approximately 20% to approximately 60%, of the active substance. Pharmaceutical preparations according to the invention for enteral or parenteral administration are, for example, those in dosage unit forms, such as dragées, tablets, capsules or suppositories, or also ampoules. These are produced in a manner known per se, for example by means of conventional mixing, granulating, coating, dissolving or lyophilising processes. Thus, pharmaceutical preparations for oral administration can be obtained by combining the active substance with solid carriers, optionally granulating a resulting mixture, and processing the mixture or granulate to form tablets or dragée cores, if desired or necessary after the addition of suitable adjuncts.

Suitable carriers are especially fillers, such as sugars, for example lactose, saccharose, mannitol or sorbitol, cellulose preparations and/or calcium phosphates, for example tricalcium phosphate or calcium hydrogen phosphate, also binders, such as starch pastes using, for example, corn, wheat, rice or potato starch, gelatin, tragacanth, methylcellulose and/or polyvinylpyrrolidone, and/or, if desired, disintegrators, such as the above-mentioned starches, and also carboxymethyl starch, cross-linked polyvinylpyrrolidone, agar, alginic acid or a salt thereof, such as sodium alginate. Adjuncts are especially flow-regulating agents and lubricants, for example silica, talc, stearic acid or salts thereof, such as magnesium or calcium stearate, and/or polyethylene glycol. Dragée cores are provided with suitable, optionally gastric juice-resistant, coatings, there being used, inter alia, concentrated sugar solutions, which optionally contain gum arabic, talc, polyvinylpyrrolidone, polyethylene glycol and/or titanium dioxide, lacquer solutions in suitable organic solvents or solvent mixtures, or, to produce gastric juice-resistant coatings, solutions of suitable cellulose preparations, such as acetylcellulose phthalate or hydroxypropylmethylcellulose phthalate. Colouring matter or pigments may be added to the tablets or dragée coatings, for example for identification purposes or for indicating different doses of active substance.

Other pharmaceutical preparations for oral administration are dry-filled capsules made of gelatin, and soft sealed capsules consisting of gelatin and a plasticiser, such as glycerin or sorbitol. The dry-filled capsules may contain the active substance in the form of a granulate, for example in admixture with fillers, such as lactose, binders, such as starches, and/or glidants, such as talc or magnesium stearate, and optionally stabilisers. In soft capsules the active substance is preferably dissolved or suspended in suitable liquids, such as fatty oils, paraffin oil or liquid polyethylene glycols, it likewise being possible for stabilisers to be added.

There come into consideration as rectally administrable pharmaceutical preparations, for example suppositories consisting of a combination of the active substance with a suppository base. Suitable suppository bases are, for example, natural or synthetic triglycerides, paraffin hydrocarbons, polyethylene glycols or higher alkanols. It is also possible to use gelatin rectal capsules that contain a combination of the active substance with a base, there coming into consideration as base substances, for example liquid triglycerides, polyethylene glycols or paraffin hydrocarbons.

Especially suitable forms for parenteral administration are aqueous solutions of an active substance in water-soluble form, for example a water-soluble salt, or suspensions of the active substance, such as corresponding oily injection suspensions, suitable lipophilic solvents or vehicles, such as fatty oils, for example sesame oil, or synthetic fatty acid esters, for example ethyl oleate or triglycerides, being used, or aqueous injection suspensions that contain viscosity-increasing substances, for example sodium carboxymethylcellulose, sorbitol and/or dextran and optionally also stabilisers.

Tinctures and solutions usually have an aqueous ethanolic base, to which there are added, inter alia, polyalcohols, for example glycerin, glycols and/or polyethylene glycol, as moisture-retaining agents for reducing evaporation, and fat-restoring substances, such as fatty acid esters with low polyethylene glycols, that is to say lipophilic substances soluble in aqueous mixture as a replacement for the fatty substances removed from the skin by the alcohol, and, if necessary, other adjuncts and additives.

The present invention relates also to the use of the compounds of the formulae I and II and the salts of such compounds with salt-forming properties, preferably for combating parasitising helminths, especially those of the families mentioned above.

The following Examples illustrate the above-described invention but are in no way intended to limit the scope thereof. Temperatures are in degrees Centigrade.

EXAMPLE 1

70 g (0.28 mole) of 2-tert.-butyl-6-isothiocyanobenzthiazole are dissolved in 1200 ml of ether and 33 g (0.33 mole) of 4-methylpiperazine are added dropwise, while stirring. The mixture is stirred for 1 hour, filtered and washed first with ether, then with petroleum ether. 2-tert.-butyl-6-[(4-methylpiperazin-1-yl)-thiocarbonylamino]-benzthiazole having a melting point of 176–177° is obtained:

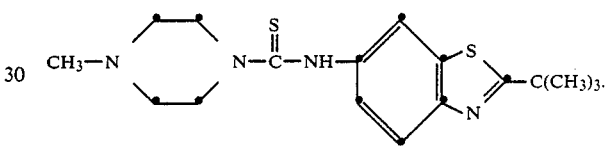

The following compounds can be produced in an analogous manner:

2-tert.-butyl-5-methoxy-6-[(4-methylpiperazin-1-yl)-thiocarbonylamino]-benzthiazole, m.p. 150–151°, 2-tert.-butyl-5-chloro-6-[(4-methylpiperazin-1-yl)-thiocarbonylamino]-benzthiazole, m.p. 158–160°, and 2-tert.-butyl-5-methyl-6-[(4-methylpiperazin-1-yl)-thiocarbonylamino]-benzthiazole, m.p. 185–187°.

EXAMPLE 2

4.33 g (0.183 mole) of sodium are dissolved in 300 ml of ethanol under nitrogen. Then, 17,6 g (0.094 mole) of N-methylpiperazine-N-oxide-dihydrochloride are added. After 15 minutes the sodium chloride formed is filtered off and washed with ethanol. The filtrate is introduced dropwise into a suspension of 24 g (0.085 mole) of 2-tert.-butyl-6-isothiocyano-5-methyl-benzthiazole in 120 ml of ethanol at room temperature. The mixture is then stirred for 2 hours and the ethanol is distilled off in vacuo. The residue is extracted with water and methylene chloride. The methylene chloride base (100 ml) is separated off, dried with sodium sulphate, filtered, diluted with 100 ml of petroleum ether and cooled to 0°. After filtration, 2-tert.-butyl-5-methyl-6-[(4-methyl-4-oxido-piperazin-1-yl)-thiocarbonylamino]-benzthiazole having a melting point of 129–131° is obtained.

The following compounds can be produced in an analogous manner:

2-tert.-butyl-5-methoxy-6-[(4-methyl-4-oxido-piperazin-1-yl)-thiocarbonylamino]-benzthiazole, m.p. 144°, 2-tert.-butyl-5-chloro-6-[(4-methyl-4-oxido-piperazin-1-yl)-thiocarbonylamino]-benzthiazole, m.p. 119–121°.

EXAMPLE 3

21 g (0.076 mole) of 2-tert.-butyl-6-isothiocyano-5-methoxy-benzthiazole are dissolved in 400 ml of acetone and a solution of 12 g (0.092 mole) of N-(2-hydroxyethyl)-piperazine in 40 ml of acetone is added dropwise. The mixture is stirred for 2 hours, cooled to 0°, filtered and washed with acetone, then with ether and finally with petroleum ether. 2-tert.-butyl-5-methoxy-6-{[4-(2-hydroxyethyl)-piperazin-1-yl]-thiocarbonylamino}-benzthiazole having a melting point of 161–162° is obtained.

The following compounds can be produced in an analogous manner:

2-tert.-butyl-6-{[4-(2-hydroxyethyl)-piperazin-1-yl]-thiocarbonylamino}-benzthiazole, m.p. 172–175°, and 2-isopropyl-6-{[4-(2-hydroxyethyl)-piperazin-1-yl]-thiocarbonylamino}-benzthiazole, m.p. 172–175°.

EXAMPLE 4

27.8 g (0.10 mole) of 2-tert.-butyl-6-isothiocyano-5-methoxy-benzthiazole are dissolved in 150 ml of dimethylformamide and 14 g (0.13 mole) of 3-mercaptopropionic acid are added. The solution is stirred at room temperature under nitrogen for 2 hours, then poured onto 2 kg of ice and stirred until the product has become solid. It is filtered off, washed with water and heated in 700 ml of toluene, decanted from water, dried over sodium sulphate, clarified with active carbon and filtered. The filtrate is diluted at 30–40° with approximately 700 ml of petroleum ether and cooled slowly to 5°, filtered off and subsequently washed with petroleum ether.  N-[2-tert.-butyl-5-methoxy-benzthiazol-6-yl]-dithiocarbamic acid S-(2-carboxyethyl)-ester having a melting point of 154–156° is obtained:

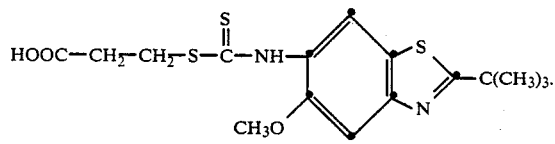

The following compounds can be produced in an analogous manner:

N-[2-tert.-butyl-benzthiazol-6-yl]-dithiocarbamic acid S-(2-carboxyethyl)-ester, m.p. 135–137°, N-[2-tert.-butyl-5-chloro-benzthiazol-6-yl]-dithiocarbamic acid S-(2-carboxyethyl)-ester, m.p. 95–97°, and N-[2-tert.-butyl-5-methyl-benzthiazol-6-yl]-dithiocarbamic acid S-(2-carboxyethyl)-ester, m.p. 155–158°.

EXAMPLE 5

Furthermore, the following can be produced in an analogous manner to those described in Examples 1–4:

N-[2-tert.-butyl-5-methoxy-benzthiazol-6-yl]-dithiocarbamic acid S-(2-carboxypropyl)-ester, m.p. 136–140°, and N-[2-tert.-butyl-5-methoxy-benzthiazol-6-yl]-thiocarbamic acid O-(2-carboxyethyl)-ester, m.p. 173–176°.

EXAMPLE 6

Furthermore, the following can be produced in an analogous manner to those described in Examples 1–4 or according to one of the methods of production described in the description for compounds of the formula I:

N-[2-tert.-butyl-5-methoxy-benzthiazol-6-yl]-thiocarbamic acid S-(2-carboxyethyl)-ester, m.p. 231–233°, 2-tert.-butyl-5-methoxy-6-[(4-methylpiperazin-1-yl)-carbonylamino]-benzthiazole, m.p. 176–179°, 2-tert.-butyl-5-methyl-6-[(4-methylpiperazin-1-yl)-thiocarbonylamino]-benzoxazole, m.p. 195–197°, 2-tert.-butyl-5-chloro-6-[(4-methylpiperazin-1-yl)-thiocarbonylamino]-benzoxazole, m.p. 181–182°, 2-tert.-butyl-5-methoxy-6-[(4-methylpiperazin-1-yl)-thiocarbonylamino]-benzoxazole, 2-tert.-butyl-5-methylthio-6-[(4-methylpiperazin-1-yl)-thiocarbonylamino]-benzoxazole, 2-tert.-butyl-6-[(4-methylpiperazin-1-yl)-thiocarbonylamino]-benzoxazole, m.p. 72–74°, 2-tert.-butyl-5-methyl-6-[(4-methyl-4-oxido-piperazin-1-yl)-thiocarbonylamino]-benzoxazole, m.p. 141–143°, 2-tert.-butyl-5-chloro-6-[(4-methyl-4-oxido-piperazin-1-yl)-thiocarbonylamino]-benzoxazole, m.p. 135–137°, 2-tert.-butyl-5-methoxy-6-[(4-methyl-4-oxido-piperazin-1-yl)-thiocarbonylamino]-benzoxazole, 2-tert.-butyl-5-methylthio-6-[(4-methyl-4-oxido-piperazin-1-yl)-thiocarbonylamino]-benzoxazole, 2-tert.-butyl-6-[(4-methyl-4-oxido-piperazin-1-yl)-thiocarbonylamino]-benzoxazole, N-[2-tert.-butyl-5-methyl-benzoxazol-6-yl]-dithiocarbamic acid S-(2-carboxyethyl)-ester, m.p. 160–163°, N-[2-tert.-butyl-5-chloro-benzoxazol-6-yl]-dithiocarbamic acid S-(2-carboxyethyl)-ester, m.p. 85–88°, N-[2-tert.-butyl-5-methoxy-benzoxazol-6-yl]-dithiocarbamic acid S-(2-carboxyethyl)-ester, m.p. 158–159°, N-[2-tert.-butyl-5-methylthio-benzoxazole-6-yl]-dithiocarbamic acid S-(2-carboxyethyl)-ester, 2-tert.-butyl-6-nitro-5-[(4-methylpiperazin-1-yl)-thiocarbonylamino]-benzoxazole, 2-tert.-butyl-5-[(4-methylpiperazin-1-yl)-thiocarbonylamino]-benzoxazole, 2-tert.-butyl-6-nitro-5-[(2-methyl-4-oxido-piperazin-1-yl)-thiocarbonylamino]-benzoxazole, 2-tert.-butyl-5-[(4-methylpiperazin-1-yl)-thiocarbonylamino]-benzoxazole, N-[2-tert.-butyl-6-nitro-benzoxazol-5-yl]-dithiocarbamic acid S-(2-carboxyethyl)-ester, N-[2-tert.-butyl-benzoxazol-5-yl]-dithiocarbamic acid S-(2-carboxyethyl)-ester, 2-tert.-butyl-5-methoxy-6-[(4-methylpiperazin-1-yl)-thiocarbonylamino]-benzimidazole, 2-tert.-butyl-1-ethoxycarbonyl-5-methoxy-6-[(4-methylpiperazin-1-yl)-thiocarbonylamino]-benzimidazole, 2-tert.-butyl-1-dimethylcarbamoyl-5-methoxy-6-[(4-methylpiperazin-1-yl)-thiocarbonylamino]-benzimidazole, 2-tert.-butyl-1-methanesulphonyl-5-methoxy-6-[(4-methylpiperazin-1-yl)-thiocarbonylamino]-benzimidazole, 2-tert.-butyl-1-methyl-5-methoxy-6-[(4-methylpiperazin-1-yl)-thiocarbonylamino]-benzimidazole, 2-tert.-butyl-1-benzyl-5-methoxy-6-[(4-methylpiperazin-1-yl)-thiocarbonylamino]-benzimidazole, 2-tert.-butyl-5-chloro-6-[(4-methylpiperazin-1-yl)-thiocarbonylamino]-benzimidazole, 2-tert.-butyl-1-ethoxycarbonyl-5-chloro-6-[(4-methylpiperazin-1-yl)-thiocarbonylamino]-benzimidazole, 2-tert.-butyl-1-dimethylcarbamoyl-5-chloro-6-[(4-methylpiperazin-1-yl)-thiocarbonylamino]-benzimidazole, 2-tert.-butyl-1-methanesulphonyl-5-chloro-6-[(4-methylpiperazin-1-yl)-thiocarbonylamino]-benzimidazole, 2-tert.-butyl-1-methyl-5-chloro-6-[(4-methylpiperazin-1-yl)-thiocarbonylamino]-benzimidazole, 2-tert.-butyl-1-benzyl-5-chloro-6-[(4-methylpiperazin-1-yl)-thiocarbonylamino]-benzimidazole, 2-tert.-butyl-6-[(4-methylpiperazin-1-yl)-thiocarbonylamino]-benzimidazole, 2-tert.-butyl-1-ethoxycarbonyl-6-[(4-methylpiperazin-1-yl)-thiocarbonylamino]-benzimidazole, 2-tert.-butyl-1-dimethylcarbamoyl-6-[(4-methylpiperazin-1-yl)-thiocarbonylamino]-benzimidazole, 2-tert.-butyl-1-methanesulphonyl-6-[(4-methylpiperazin-1-yl)-thiocarbonylamino]-benzimidazole, 2-tert.-butyl-1-methyl-6-[(4-methylpiperazin-1-yl)-thiocarbonylamino]-benzimidazole, 2-tert.-butyl-1-benzyl-6-[(4-methylpiperazin-1-yl)-thiocarbonylamino]-benzimidazole, 2-tert.-butyl-5-propylthio-6-[(4-methylpiperazin-1-yl)-thiocarbonylamino]-benzimidazole, 2-tert.-butyl-1-ethoxycarbonyl-5-propylthio-6-[(4-methylpiperazin-1-yl)-thiocarbonylamino]-benzimidazole, 2-tert.-butyl-1-dimethylcarbamoyl-5-propylthio-6-[(4-methylpiperazin-1-yl)-thiocarbonylamino]-benzimidazole, 2-tert.-butyl-1-methanesulphonyl-5-propylthio-6-[(4-methylpiperazin-1-yl)-thiocarbonylamino]-benzimidazole, 2-tert.-butyl-1-methyl-5-propylthio-6-[(4-methylpiperazin-1-yl)-thiocarbonylamino]-benzimidazole, 2-tert.-butyl-1-benzyl-5-propylthio-6-[(2-methylpiperazin-1-yl)-thiocarbonylamino]-benzimidazole, 2-tert.-butyl-5-methoxy-6-[(4-methyl-4-oxido-piperazin-1-yl)-thiocarbonylamino]-benzimidazole, 2-tert.-butyl-1-ethoxycarbonyl-5-methoxy-6-[(4-methyl-4-oxido-piperazin-1-yl)-thiocarbonylamino]-benzimidazole, 2-tert.-butyl-1-dimethylcarbamoyl-5-methoxy-6-[(4-methyl-4-oxido-piperazin-1-yl)-thiocarbonylamino]-benzimidazole, 2-tert.-butyl-1-methanesulphonyl-5-methoxy-6-[(4-methyl-4-oxido-piperazin-1yl)-thiocarbonylamino]-benzimidazole, 2-tert.-butyl-1-methyl-5-methoxy-6-[(4-methyl-4-oxido-piperazin-1-yl)-thiocarbonylamino]-benzimidazole, 2-tert.-butyl-1-benzyl-5-methoxy-6-[(4-methyl-4-oxido-piperazin-1-yl)-thiocarbonylamino]-benzimidazole 2-tert.-butyl-5-chloro-6-[(4-methyl-4-oxido-piperazin-1-yl)-thiocarbonylamino]-benzimidazole, 2-tert.-butyl-1-ethoxycarbonyl-5-chloro-6-[(4-methyl-4-oxido-piperazin-1-yl)-thiocarbonylamino]-benzimidazole, 2-tert.-butyl-1-dimethylcarbamoyl-5-chloro-6-[(4-methyl-4-oxido-piperazin-1-yl)-thiocarbonylamino]-benzimidazole, 2-tert.-butyl-1-methanesulphonyl-5-chloro-6-[(4-methyl-4-oxido-piperazin-1-yl)-thiocarbonylamino]-benzimidazole, 2-tert.-butyl-1-methyl-5-chloro-6-[(4-methyl-4-oxido-piperazin-1-yl)-thiocarbonylamino]-benzimidazole, 2-tert.-butyl-1-benzyl-5-chloro-6-[(4-methyl-4-oxido-piperazin-1-yl)-thiocarbonylamino]-benzimidazole, 2-tert.-butyl-5-propylthio-6-[(1-methyl-4-oxido-piperazin-1-yl)-thiocarbonylamino]-benzimidazole, 2-tert.-butyl-1-ethoxycarbonyl-5-propylthio-6-[(1-methyl-4-oxido-piperazin-1-yl)-thiocarbonylamino]-benzimidazole, 2-tert.-butyl-1-dimethylcarbamoyl-5-propylthio-6-[(1-methyl-4-oxido-piperazin-1-yl)-thiocarbonylamino]-benzimidazole, 2-tert.-butyl-1-methanesulphonyl-5-propylthio-6-[(1-methyl-4-oxido-piperazin-1-yl)-thiocarbonylamino]-benzimidazole, 2-tert.-butyl-1-methyl-5-propylthio-6-[(1-methyl-4-oxido-piperazin-1-yl)-thiocarbonylamino]-benzimidazole, 2-tert.-butyl-1-benzyl-5-propylthio-6-[(1-methyl-4-oxido-piperazin-1-yl)-thiocarbonylamino]-benzimidazole, 2-tert.-butyl-6-[(4-methyl-4-oxido-piperazin-1-yl)-thiocarbonylamino]-benzimidazole, 2-tert.-butyl-1-ethoxycarbonyl-6-[(4-methyl-4-oxido-piperazin-1-yl)-thiocarbonylamino]-benzimidazole, 2-tert.-butyl-1-dimethylcarbamoyl-6-[(4-methyl-4-oxido-piperazin-1-yl)-thiocarbonylamino]-benzimidazole, 2-tert.-butyl-1-methanesulphonyl-6-[(4-methyl-4-oxido-piperazin-1-yl)-thiocarbonylamino]-benzimidazole, 2-tert.-butyl-1-methyl-6-[(4-methyl-4-oxido-piperazin-1-yl)-thiocarbonylamino]-benzimidazole, 2-tert.-butyl-1-benzyl-6-[(4-methyl-4-oxido-piperazin-1-yl)-thiocarbonylamino]-benzimidazole, N-[2-tert.-butyl-5-methoxy-benzimidazol-6-yl]-dithiocarbamic acid S-(2-carboxyethyl)-ester, N-[2-tert.-butyl-1-ethoxycarbonyl-5-methoxy-benzimidazol-6-yl]-dithiocarbamic acid S-(2-carboxyethyl)-ester, N-[2-tert.-butyl-1-dimethylcarbamoyl-5-methoxy-benzimidazol-6-yl]-dithiocarbamic acid S-(2-carboxyethyl)-ester, N-[2-tert.-butyl-1-methanesulphonyl-5-methoxy-benzimidazol-6-yl]-dithiocarbamic acid S-(2-carboxyethyl)-ester, N-[2-tert.-butyl-1-methyl-5-methoxy-benzimidazol-6-yl]-dithiocarbamic acid S-(2-carboxyethyl)-ester, N-[2-tert.-butyl-1-benzyl-5-methoxy-benzimidazol-6-yl]-dithiocarbamic acid S-(2-carboxyethyl)-ester, N-[2-tert.-butyl-5-chloro-benzimidazol-6-yl]-dithiocarbamic acid S-(2-carboxyethyl)-ester, N-[2-tert.-butyl-1-ethoxycarbonyl-5-chloro-benzimidazol-6-yl]-dithiocarbamic acid S-(2-carboxyethyl)-ester, N-[2-tert.-butyl-1-dimethylcarbamoyl-5-chloro-benzimidazol-6-yl]-dithiocarbamic acid S-(2-carboxyethyl)-ester, N-[2-tert.-butyl-1-methanesulphonyl-5-chloro-benzimidazol-6-yl]-dithiocarbamic acid S-(2-carboxyethyl)-ester, N-[2-tert.-butyl-1-methyl-5-chloro-benzimidazol-6-yl]-dithiocarbamic acid S-(2-carboxyethyl)-ester, N-[2-tert.-butyl-1-benzyl-5-chloro-benzimidazol-6-yl]-dithiocarbamic acid S-(2-carboxyethyl)-ester, N-[2-tert.-butyl-5-propylthio-benzimidazol-6-yl]-dithiocarbamic acid S-(2-carboxyethyl)-ester, N-[2-tert.-butyl-1-ethoxycarbonyl-5-propylthio-benzimidazol-6-yl]-dithiocarbamic acid S-(2-carboxyethyl)-ester, N-[2-tert.-butyl-1-dimethylcarbamoyl-5-propylthi-obenzimidazol-6-yl]-dithiocarbamic acid S-(2-carboxyethyl)-ester, N-[2-tert.-butyl-1-methanesulphonyl-5-propylthio-benzimidazol-6-yl]-dithiocarbamic acid S-(2-carboxyethyl)-ester, N-[2-tert.-butyl-1-methyl-5-propylthio-benzimidazol-6-yl]-dithiocarbamic acid S-(2-carboxyethyl)-ester, N-[2-tert.-butyl-1-benzyl-5-propylthio-benzimidazol-6-yl]-dithiocarbamic acid S-(2-carboxyethyl)-ester, N-[2-tert.-butyl-benzimidazol-6-yl]-dithiocarbamic acid S-(2-carboxyethyl)-ester, N-[2-tert.-butyl-1-ethoxycarbonyl-benzimidazol-6-yl]-dithiocarbamic acid S-(2-carboxyethyl)-ester, N-[2-tert.-butyl-1-dimethylcarbamoyl-benzimidazol-6-yl]-dithiocarbamic acid S-(2-carboxyethyl)-ester, N-[2-tert.-butyl-1-methanesulphonyl-benzimidazol-6-yl]-dithiocarbamic acid S-(2-carboxyethyl)-ester, N-[2-tert.-butyl-1-methyl-benzimidazol-6-yl]-dithiocarbamic acid S-(2-carboxyethyl)-ester, N-[2-tert.-butyl-1-benzyl-benzimidazol-6-yl]-dithiocarbamic acid S-(2-carboxyethyl)-ester, N-[2-isopropyl-benzimidazol-5-yl]-dithiocarbamic acid S-(2-carboxyethyl)-ester, m.p. 112°–115°, N-[2-isopropyl-6-(4-methyl-piperazin-1-yl)-thiocarbonylamino]-benzimidazole, m.p. 144°–147°, N-[2-isopropyl-5-methyl-benzoxazol-6-yl]-dithiocarbamic acid S-(2-carboxyethyl)-ester, m.p. 142°–146°, N-[2-tert.-butyl-benzoxazol-6-yl]-dithiocarbamic acid S-(2-carboxyethyl)-ester, m.p. 150°–155°, N-[2-isopropyl-benzoxazol-6-yl]-dithiocarbamic acid S-(2-carboxyethyl)-ester, m.p. 168°–174°, N-[2-isopropyl-benzthiazol-6-yl]-dithiocarbamic acid S-(2-carboxyethyl)-ester, m.p. 165°–168°, N-[2-isopropyl-5-methoxy-benzthiazol-6-yl]-dithiocarbamic acid S-(2-carboxyethyl)-ester, m.p. 126°–129°, N-[2-tert.-butyl-5,7-dimethyl-benzthiazol-6-yl]-dithiocarbamic acid S-(2-carboxyethyl)-ester, m.p. 170°–173°, and 2-tert.-butyl-6-[(4-methyl-4-oxido-piperazin-1-yl)-thiocarbonylamino)-benzthiazole.

EXAMPLE 7

Tablets containing 2-tert.-butyl-6-[(4-methylpiperazin-1-yl)-thiocarbonylamino]-benzthiazole can be produced as follows:

| Composition (for 10000 tablets) | |
|---|---|
| 2-tert.-butyl-6-[(4-methylpiperazin-1-yl)-thiocarbonylamino]-benzthiazole | 5000 g |
| wheat starch | 790 g |
| stearic acid | 30 g |
| magnesium stearate | 30 g |
| talc | 400 g |
| water | q.s. |

A mixture of the 2-tert.-butyl-6-[(4-methylpiperazin-1-yl)-thiocarbonylamino]-benzthiazole and 500 g of wheat starch is made into a paste with approximately 1300 g of demineralised water and moistened uniformly with a further 600 g of demineralised water. The mixture is kneaded to a slightly plastic composition and forced through a sieve having a mesh width of approximately 3 mm. The granulate is then dried and forced through a sieve again. The magnesium stearate, the stearic acid, the talc and 290 g of the wheat starch are then admixed with the dry granulate, which has been brought to a uniform particle size, and the mixture is pressed into tablets each weighing 0.625 g.

It is also possible to produce, in an analogous manner, tablets containing a different compound according to Example 1, or a compound according to Examples 2 to 5, as active substance.

EXAMPLE 8

In an analogous manner to that described in Example 7 it is also possible to produce tablets containing one of the compounds mentioned in Example 6.

We claim:

1. A compound of the formula

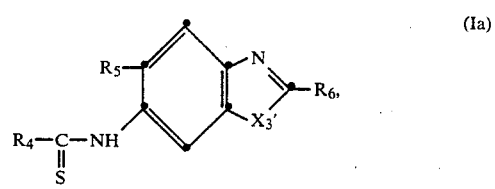

(Ia)

in which

R$_4$ represents 1-(4-lower alkyl)-piperazino having up to and including 4 C-atoms in the lower alkyl moiety, 1-(4-lower alkyl-4-oxido)-piperazino having up to and including 4 C-atoms in the lower alkyl moiety, or 1-[4-(hydroxy-lower alkyl)]-piperazino in which the hydroxy group is bonded in a position higher than the alpha-position and hydroxy-lower alkyl has up to and including 4 C-atoms and in which R$_5$ represents hydrogen, lower alkyl having up to and including 4 C-atoms, lower alkoxy having up to and including 4 C-atoms, or halogen having an atomic number of up to and including 35, X$_3$' represents oxy, thio, and R$_6$ represents alpha-branched lower alkyl having up to and including 4 C-atoms or straight-chain lower alkyl having up to and including 4 C-atoms bonded by a secondary C-atom, or a salt thereof.

2. A compound according to claim 1 of the formula

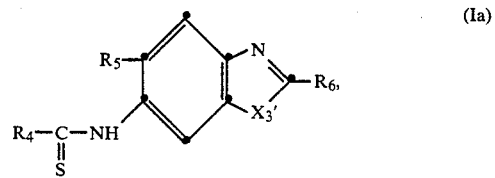

(Ia)

in which R$_4$ represents, 1-(4-methyl)-piperazino, 1-(4-methyl-4-oxido)-piperazino, or 1-[4-(2-hydroxy-ethyl)]-piperazino, and in which R$_5$ represents hydrogen, lower alkyl having up to and including 4 C-atoms, lower alkoxy having up to and including 4 C-atoms, or halogen having an atomic number up up to and including 35, X$_3$ represents thio and R$_6$ represents alpha-branched lower alkyl having up to and including 4 C-atoms or straight-chain lower alkyl having up to and including 4 C-atoms bonded by a secondary C-atom, or a salt thereof.

3. A compound according to claim 1 of the formula (Ia)

$$R_4-\underset{\underset{S}{\|}}{C}-NH-\text{[benzothiazole ring with }R_5, N, R_6, X_3'\text{]}$$

in which R₄ represents, 1-(4-methyl)-piperazino, and in which R₅ represents hydrogen, lower alkoxy or lower alkyl, each having up to and including 4 C-atoms, $X_3'$ represents thio and R₆ represents alpha-branched lower alkyl having up to and including 4 C-atoms, or a salt thereof.

4. A compound as claimed in claim 1 being 2-tert.-butyl-6-[(4-methylpiperazin-1-yl)-thiocarbonylamino]-benzthiazole or a pharmaceutically acceptable salt thereof.

5. A compound as claimed in claim 1 being 2-tert.-butyl-5-methoxy-6-[(4-methylpiperazin-1-yl)-thiocarbonylamino]-benzthiazole or a pharmaceutically acceptable salt thereof.

6. A compound as claimed in claim 1 being 2-tert.-butyl-5-chloro-6-[(4-methylpiperazin-1-yl)-thiocarbonylamino]-benzthiazole or a pharmaceutically acceptable salt thereof.

7. A compound as claimed in claim 1 being 2-tert.-butyl-5-methyl-6-[(4-methylpiperazin-1-yl)-thiocarbonylamino]-benzthiazole or a pharmaceutically acceptable salt thereof.

8. A compound as claimed in claim 1 being 2-tert.-butyl-6-[(4-methyl-4-oxido-piperazin-1-yl)-thiocarbonylamino]-benzthiazole or a pharmaceutically acceptable salt thereof.

9. A compound as claimed in claim 1 being 2-tert.-butyl-5-methoxy-6-[(4-methyl-4-oxido-piperazin-1-yl)-thiocarbonylacylamino]-benzthiazole or a pharmaceutically acceptable salt thereof.

10. A compound as claimed in claim 1 being 2-tert.-butyl-5-chloro-6-[(4-methyl-4-oxido-piperazin-1-yl)-thiocarbonylamino]-benzthiazole or a pharmaceutically acceptable salt thereof.

11. A compound as claimed in claim 1 being 2-tert.-butyl-5-methyl-6-[(4-methyl-4-oxido-piperazin-1-yl)-thiocarbonylamino]-benzthiazole or a pharmaceutically acceptable salt thereof.

12. A compound as claimed in claim 1 being 2-tert.-butyl-5-methoxy-6-{[4-(2-hydroxyethyl)-piperazin-1-yl]-thiocarbonylamino}-benzthiazole or a pharmaceutically acceptable salt thereof.

13. A compound as claimed in claim 1 being 2-tert.-butyl-6-{[4-(2-hydroxyethyl)-piperazin-1-yl]-thiocarbonyl-amino}-benzthiazole or a pharmaceutically acceptable salt thereof.

14. A compound as claimed in claim 1 being 2-isopropyl-6-{[4-(2-hydroxyethyl)-piperazin-1-yl]-thiocarbonylamino}-benzthiazole or a pharmaceutically acceptable salt thereof.

15. A compound claimed in claim 1 being 2-tert.-butyl-5-methoxy-6-[(4-methylpiperazin-1-yl)-carbonylamino]-benzthiazole or a pharmaceutically acceptable salt thereof.

16. A compound claimed in claim 1 being 2-tert.-butyl-5-methyl-6-[(4-methylpiperazin-1-yl)-thiocarbonylamino]-benzoxazole or a pharmaceutically acceptable salt thereof.

17. A compound claimed in claim 1 being 2-tert.-butyl-chloro-6-[(4-methylpiperazin-1-yl)-thiocarbonylamino]-benzoxazole or a pharmaceutically acceptable salt thereof.

18. A compound claimed in claim 1 being 2-tert.-butyl-[(4-methylpiperazin-1-yl)-thiocarbonylamino]-benzoxazole a pharmaceutically acceptable salt thereof.

19. A compound claimed in claim 1 being 2-tert.-butyl-5-methyl-6-[(4-methyl-4-oxido-piperazin-1-yl)-thiocarbonyl-amino]-benzoxazole or a pharmaceutically acceptable salt thereof.

20. A compound claimed in claim 1 being 2-tert.-butyl-5-chloro-6-[(4-methyl-4-oxido-piperazin-1-yl)-thiocarbonylamino]-benzoxazole or a pharmaceutically acceptable salt thereof.

21. A compound claimed in claim 1 being N-[2-isopropyl-6-(4-methyl-piperazin-1-yl)-thiocarbonylamino]-benzimidazole or a pharmaceutically acceptable salt thereof.

22. A compound claimed in claim 1 being 2-tert.-butyl-6-[(4-methyl-4-oxido-piperazin-1-yl)-thiocarbonylamino]-benzthiazole or a pharmaceutically salt thereof.

23. A pharmaceutical composition preparation containing an anthelmintically effective amount of a compound according to claim 1 in admixture with customary pharmaceutical auxilliaries and/or carriers.

24. A method of combatting parasitic helminths in a warm-blooded organisms characterised in that an anthelmintically effective amount of a compound according to claim 1 or of a pharmaceutical by acceptable salt thereof is administered.

25. Compounds of the formula $$R_1-\underset{\underset{\|}{X_1}}{C}-NH-Ph\underset{X_3}{\overset{N}{\diagup\diagdown}}R_3,\quad(I)$$

in which
R₁ represents 1-(4-lower alkyl)-piperazino, 1-(4-lower alkyl-4-oxido)-piperazino or 1-[4-(hydroxy-lower alkyl)]-piperazino, wherein the hydroxy group is bonded in a position higher than the alpha-position,
$X_1$ represents oxygen or sulphur,
Ph represents 1,2-phenylene optionally further mono- or di-substituted by lower alkyl, lower alkoxy, lower alkanoyl, trifluoromethyl and/or halogen,
$X_3$ represents oxygen or sulphur and
R₃ represents optionally fluorine-substituted lower alkyl or 3- or 8-membered cycloalkyl,
or a salt, thereof.

* * * * *

UNITED STATES PATENT AND TRADEMARK OFFICE
CERTIFICATE OF CORRECTION

PATENT NO. : 4,511,567
DATED : April 16, 1985
INVENTOR(S) : Jean J. Gallay and Ernst Schweizer It is certified that error appears in the above-identified patent and that said Letters Patent is hereby corrected as shown below:

Claim 17, Column 28, Line 8 should read-- butyl-5-chloro-6-[(4-methylpiperazin-1-yl)-thiocar-  --.

Claim 18, Column 28, Line 12 should read-- butyl-6-[(4-methylpiperazin-1-yl)-thiocarbonylamino]-  --.

Signed and Sealed this

Twelfth Day of November 1985

[SEAL]

Attest:

DONALD J. QUIGG

Attesting Officer

Commissioner of Patents and Trademarks